United States Patent
Bell et al.

(10) Patent No.: US 6,399,645 B1
(45) Date of Patent: Jun. 4, 2002

(54) CHEMOPREVENTION AND TREATMENT OF CERVICAL OR VAGINAL NEOPLASIA

(76) Inventors: Maria Bell; Delf-Christian Schmidt-Grimminger, both of 562 Tolland Dr., Castle Rock, CO (US) 80104

(*) Notice: Subject to any disclaimer, the term of this patent is extended or adjusted under 35 U.S.C. 154(b) by 0 days.

(21) Appl. No.: 09/531,031

(22) Filed: Mar. 20, 2000

(51) Int. Cl.[7] .................. A61K 31/40; A61K 31/405
(52) U.S. Cl. ............................. 514/414; 514/415
(58) Field of Search ...................... 514/414, 415

(56) References Cited

U.S. PATENT DOCUMENTS

| | | | |
|---|---|---|---|
| 5,356,928 A | 10/1994 | Murray et al. | 514/415 |
| 5,895,787 A | 4/1999 | Arffmann et al. | 514/415 |
| 5,948,808 A * | 9/1999 | Safe | 514/415 |

OTHER PUBLICATIONS

Wattenberg et al., Cancer Research, vol. 38, pp 1410–1413, May 1978.*
Husseinzadeh, N., et al., Subclinical Cervicovaginal Human Papillomavirus Infections Associated with Cervical Condylomata and Dysplasia Treatment Outcomes, *J. Reprod. Med.*, vol. 39 777–80, (1994).
World Health Organization, The World Health Report, Geneva: WHO, (1997).
Richart, R., Causes and Management of Cervical Intraepithelial Neoplasis, vol. 60, *Cancer*, 1951–1959, (1987).
Epidemiologic Evidence Showing that Human Papillomavirus Infection Causes Most Cervical Intraepithelia Neoplasia, vol. 85, *J. Natl. Cancer Inst.*, 958–964 (1993).
Barron, B. & Richart, R., AStatistical Model of the Natural History of Cervical Carcinoma, II. Estimates of the Transition Time from Dysplasia to Carcinoma In Situ, vol. 45, *J. Natl Cancer Inst.*, 1025, (1970).
Wattenberg, L.W. & Loub, W.D., AInhibition of Polycyclic Aromatic Hydrocarbon–Induced Neoplasia by Naturally Occurring Indoles, vol. 38, *Cancer Res.*, 1410–1413, (1978).

Grubbs C.J., et al., Chemoprevention of Chemically–Induced Mammary Carcinogenesis by Indole–3–Carbinol, vol. 15, *Anticancer Res.*, 709–718, (1995).
New field et al., Estrogen Metabolism & Human Papillmavirus–Induced Tumors of the Larynx: Chemo–Prophylaxis with Indole–3–Carbinol, vol. 13, *Anticancer Res.*, 337–342, (1993).
Coll, D. et al., Treatment of Recurrent Respiratory Papillomatosis with Indole–3–Carbinol, vol. 18 *Am. J. Otolaryngol.*, 283–285, (1997).
Chase et al., Remington's Pharmaceutical Sciences (16.sup.th ed., Mack Publishing Co., Easton, Pa, USA 1980).
Sepkovic, et al., Estrogen Metabolite Ratios and Rist Assessment of Hormone–related Cancers *Annals New York Academy of Sciences*, (312–314), 1995.
Rosen, et al., Preliminary Result of the Use of Indole–3–Carbinol for Recurrent Respiratory Papillomatosis, *Otolaryngology—Head & Neck Surgery*, 118(6): 810–5, Jun. 1998.
Michnovicz, J.J., et al., Changes in Levels of Urinary Estrogen Metabolites after Oral Indole–3–Carbinol Treatment in Humans ©, 1997.
Jin, L., et al., Indole–3–Carbinol Prevents Cervical Cancer in Human Papilloma Virus Type 16 (HPV16) Transgenic Mice, *Cancer Research*, 1999.
Parazzini, et al. The Epidemiology of Endometrial Cancer, Gynecologic ONcology 41, –16 (1999).

* cited by examiner

*Primary Examiner*—Jerome D. Goldberg
(74) *Attorney, Agent, or Firm*—Dorsey & Whitney LLP (57) ABSTRACT

The invention relates to non-surgical methods for treating cervical or vaginal neoplasia including cervical intraepithelial neoplasia, intraepithelial neoplasia, vulvar intraepithelial neoplasia and ano-genital warts. The treatment, which utilizes an effective amount of indole-3-carbinol and/or diindolylmethane, is effective whether or not the patient is also infected with human papillomavirus, the most common sexually transmitted viral disease in the United States and a known risk factor for both cervical intraepithelial neoplasia and cervical cancer.

16 Claims, 4 Drawing Sheets

FIGURE 1

Indole-3-Carbinol (I3C)

FIGURE 2

Diindolylmethane (DIM)

FIGURE 3

(Regression of CIN compared to dose of indole-3-carbinol.)

FIGURE 4

CHEMOPREVENTION AND TREATMENT OF CERVICAL OR VAGINAL NEOPLASIA

I. FIELD OF THE INVENTION

This invention relates to the treatment of cervical or vaginal neoplasia including cervical intraepithelial neoplasia ("CIN"), intraepithelial neoplasia, vulvar intraepithelial neoplasia and ano-genital warts, and in particular, provides a method of treatment to prevent these conditions from progressing into cancer. Treatment in accordance with the present invention utilizes an effective amount of indole-3-carbinol ("I3C") and/or diindolylmethane ("DIM").

II. BACKGROUND OF THE INVENTION

Human papillomavirus ("HPV") infection of the lower genital tract is the most common sexually transmitted viral disease in the United States. (Husseinzadeh, N., et al., "Subclinical Cervicovaginal Human Papillomavirus Infections Associated with Cervical Condylomata and Dysplasia Treatment Outcomes," *J. Reprod. Med.*, Vol. 39, 777-80, (1994)). Most of these viral infections remain dormant and never result in clinically evident disease. However, in some cases, the virus may propagate and cause clinically recognizable HPV-associated changes, including condylomata (genital warts), precancerous lesions of the cervix, as well as invasive cervical cancer. Cancer of the cervix is the second most common cancer in women and the seventh most common form of cancer worldwide. (World Health Organization, "The World Health Report," Geneva: WHO, (1997)). The association between HPV infection and genital cancer is well documented. (Richart, R., "Causes and Management of Cervical Intraepithelial Neoplasia," Vol. 60, *Cancer*, 1951-1959, (1987); Schiffman, M. et al., "Epidemiologic Evidence Showing that Human Papillomavirus Infection Causes Most Cervical Intraepithelial Neoplasia," Vol. 85, *J. Nat'l Cancer Inst.*, 958–964, (1993)).

Not all dysplastic lesions develop into cancer. Mildly dysplastic lesions will spontaneously regress without therapy in the majority of patients, and only a small subset of cases actually possess cancerous potential. Less than one half of more severely dysplastic lesions in patients will eventually progress to invasive disease. (Barron, B. & Richart, R., "Statistical Model of the Natural History of Cervical Carcinoma. II. Estimates of the Transition Time from Dysplasia to Carcinoma In Situ," Vol. 45, *J. Nat'l Cancer Inst.*, 1025, (1970)). The progression of HPV infection to genital cancer is therefore not absolute, and other factors (e.g., smoking, diet, and immunosuppression) probably contribute to the progression.

There is currently no available test that can accurately predict the clinical behavior of a cervical lesion. Therefore, most high-grade lesions are treated with surgical excision or ablative therapy. Chemoprevention is the attempt to use natural and synthetic compounds to intervene in the early precancerous stages of carcinogenesis, before invasive disease begins. There is currently no chemopreventative therapy that prevents or impedes the progression of CIN, intraepithelial neoplasia, vulvar intraepithelial neoplasia and ano-genital warts to cancer.

Many families of fruits and vegetables contain relatively high concentrations of unique phytochemicals with potential cancer-preventing properties. As a general matter, diets high in cruciferous vegetables (e.g., broccoli, cabbage, cauliflower, bok-choi, and brussels sprouts) can retard cancer growth in animals and increased consumption of these vegetables by humans has been associated with decreased cancers of the colon, lung, and breast. (Wattenberg, L. W. & Loub, W. D., "Inhibition of Polycyclic Aromatic Hydrocarbon-Induced Neoplasia by Naturally Occurring Indoles," Vol. 38, *Cancer Res.*, 1410–1413, (1978)). The specific method of action, however, has not been identified. It has been observed that a specific compound found in crucifers, indole-3-carbinol ("I3C"), may be able to prevent or halt carcinogenesis in certain cases. (Grubbs C. J. et al., "Chemoprevention of Chemically-Induced Mammary Carcinogenesis by Indole-3-Carbinol," Vol. 15, *Anticancer Res.*, 709–716, (1995)). Grubbs et al. showed that I3C was effective in inhibiting mammary carcinogenesis in a rat model. Newfield et al. showed that I3C inhibits growth of HPV-induced benign tumors of laryngeal tissue in a mouse model. (Newfield et al., "Estrogen Metabolism & Human Papillmavirus-Induced Tumors of the Larynx: Chemo-Prophylaxis with Indole-3-Carbinol," Vol. 13, *Anticancer Res.*, 337–341, (1993)). Although Newfield et al. suggested the possibility that a diet high in cruciferous vegetables or the consumption of an I3C supplement could perhaps be used to prevent human papillomavirus-induced tumors of the larynx or genital tract, no evidence was presented that I3C would effectively treat CIN in either mice or humans. (Newfield et al., at 340). It is well known that work in animals on one form of cancer is not predictive of the efficacy of that agent to impede or cure cancer of another form in humans.

Similarly, I3C has been used as a dietary supplement for humans to aid in the inhibition of laryngeal papillomatosis. (Coll, D. et al., "Treatment of Recurrent Respiratory Papillomatosis with Indole-3-Carbinol," Vol. 18, *Am. J. Otolaryngol.*, 283–285, (1997)). However, Coll provides no evidence that I3C would treat CIN or other forms of cervical or vaginal neoplasia in humans.

III. SUMMARY OF THE INVENTION

We have discovered that treatment of humans using a therapeutic amount of I3C is effective in the treatment of cervical intraepithelial neoplasia ("CIN"), independent of HPV infection. Roughly half of the patients with CIN experienced complete regression of the CIN after 12 weeks of daily oral administration of I3C. The use of I3C and/or DIM can be used to cause regression or to prevent the progression to cancer of other forms of cervical or vaginal neoplasia including intraepithelial neoplasia, vulvar intraepithelial neoplasia and ano-genital warts

IV. BRIEF DESCRIPTION OF THE TABLES AND DRAWINGS

Table 1 shows the regression of CIN compared to dose of I3C as described in the example herein.

Table 2 shows the change in estradiol metabolism compared to dose of I3C as described in the example herein.

V. DETAILED DESCRIPTION OF THE INVENTION AND THE PREFERRED EMBODIMENT

Figure 1:
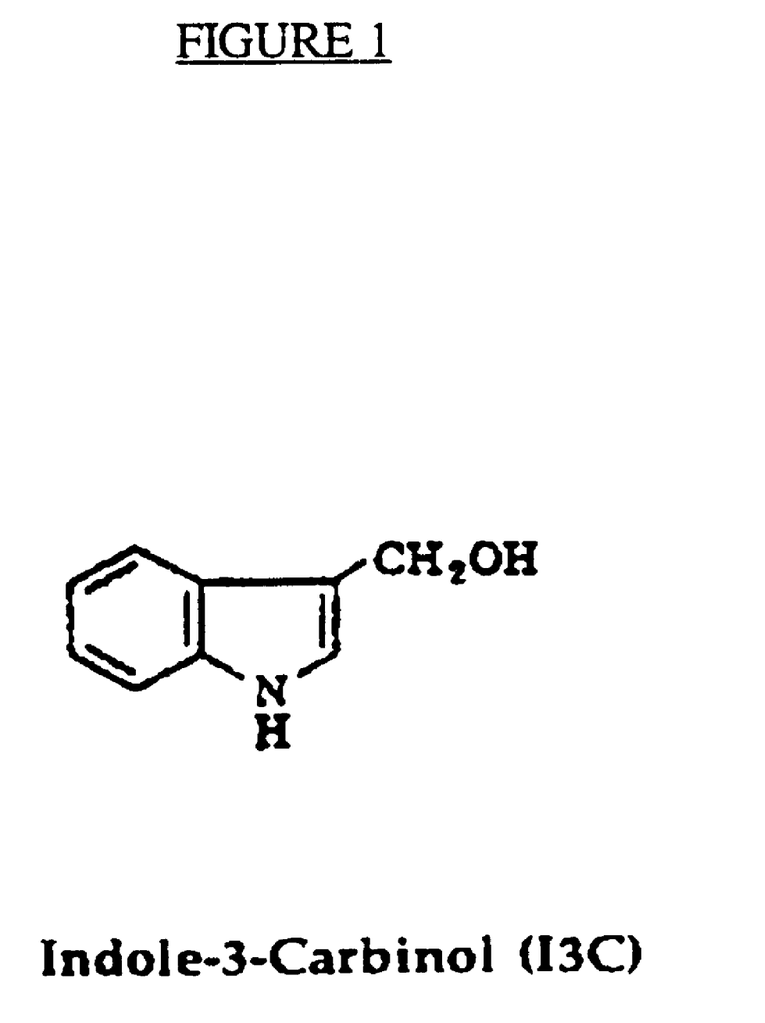
FIG. 1 shows the chemical structure of I3C.
Figure 2:
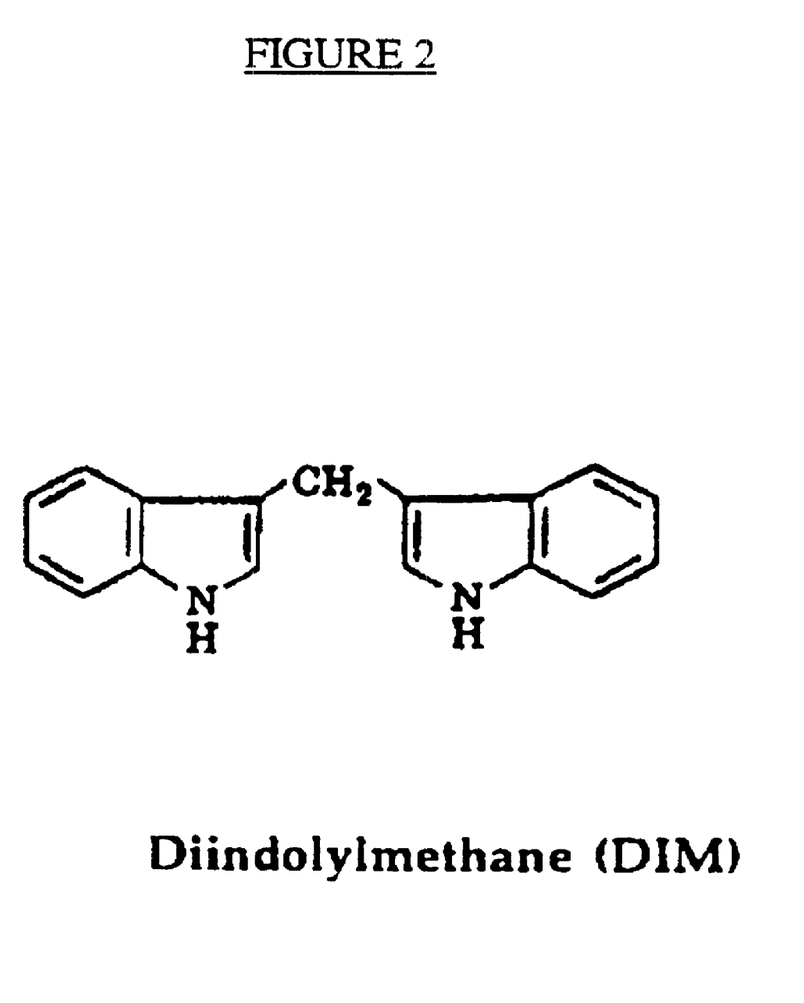
FIG. 2 shows the chemical structure of DIM.

Indole-3-carbinol, also known as 1H-indole-3-methanol, is a naturally occurring compound found in cruciferous vegetables. The chemical structure of I3C is shown in FIG. 1. Although it has been studied in connection with the prevention of certain forms of cancer, it has not been used previously in the treatment of cervical or vaginal neoplasia including cervical intraepithelial neoplasia, intraepithelial neoplasia, vulvar intraepithelial neoplasia and ano-genital warts. It has been used as a dietary supplement to aid in the inhibition of laryngeal papillomatosis. The present invention includes the chemopreventive use of I3C and/or its related compound diindolylmethane ("DIM"). The chemical structure of DIM is shown in FIG. 2.

In accordance with the present invention, I3C may be used in dosages of about 2.5 to 20 mg/kg/day administered either orally or topically. For a 70 kg individual this would translate into a dosage range of about 50 to 1400 mg/day. A preferred dosage range is about 200 to 400 mg. per day. For DIM the dosage should be in the range of about 0.5 to 20 mg/kg/day or about 50 to 150 mg. per day.

Methods and compositions for making dosage units containing the compounds are well-known to those of skill in the art. For instance, conventional techniques for making tablets and pills containing active ingredients are described in the standard reference, Chase et al., Remington's Pharmaceutical Sciences, (16.sup.th ed., Mack Publishing Co., Easton, Pa., USA, 1980) ("Remington's") at pages 1553 through 1584. Conventional techniques for coating pharmaceutical dosage forms are described at pages 1585 to 1593 of Remington's.

For making dosage units, e.g., tablets or capsules, the use of conventional additives, e.g., fillers, colorants, binders, and the like is contemplated. In general, any pharmaceutically acceptable additive which does not interfere with the function of the active compound can be used in the compositions. Suitable carriers with which the compositions can be administered include lactose, starch, cellulose derivatives and the like used in suitable amounts. Mixtures of carriers can also be used. A process of manufacturing a composition for oral administration of the invention includes mixing predetermined quantities of the active ingredient with predetermined quantities of excipients and converting the mixture into dosage units containing, for example, 200 to 400 mg, of active ingredient. Converting the mixture into dosage units generally involves molding the mixture into a tablet, filling a capsule with a dry mixture, or filling a capsule with a wet mixture.

Once made, the dosage units may be administered daily or several times a day to achieve the desired total dosage (e.g., every 6, 8 or 12 hours). Although generally less desirable from a patient acceptability view point, the active ingredient may alternatively be administered topically in dosages equivalent to the oral dosages described herein, taking into consideration effects such as bioavailability. The treatment of the present invention is effective whether or not the patient is also infected with human papillomavirus, the most common sexually transmitted viral disease in the United States, and a known risk factor for both cervical intraepithelial neoplasia and cervical cancer. Treatment in accordance with the present invention provides a non-surgical alternative to treatment of cervical intraepithelial neoplasia. Other advantages of the present invention will be recognized by one skilled in the art based on the information and data contained herein.

The invention is further explained by the following illustrative example.

VI. EXAMPLE

A. Materials and Methods

Thirty subjects with histologically confirmed CIN were enrolled. Eligibility requirements were as follows: adequate colposcopy, negative ECC, no suspicion of invasion, non-pregnant, and HIV. Table 1 contains data for the 27 patients that completed the study.

The study protocol was reviewed and approved for human research subjects by the Institutional Research Board for Human Research (IRB) of LSU Medical Center—Shreveport. Because indole-3-carbinol was available in health food stores prior to October 1994, a FDA IND number was not required.

Evaluating colposcopists and patients were blinded to the treatment. All residents and staff involved in the study were instructed regarding the protocol. The patients were randomized to placebo, 200 mg/day, or 400-mg/day treatment of indole-3-carbinol administered orally for 12 weeks. Randomization was performed by successively assigning patients from a computer-generated randomization table. Ten patients were randomized to each group; however, two patients in the 200 mg/day treatment arm and one patient in the 400-mg/day treatment arm did not complete the study. These patients were randomized, but did not return for their appointment to receive the medication and were excluded from analysis.

All patients underwent colposcopy at the initial visit as well as at their 4-week, 8-week, and 12-week visit. Photodocumentation of each colposcopic examination was obtained. At the end of the trial, each patient was reexamined, and if the patient had persistent CIN on 12-week biopsy, or if the colposcopic impression was persistent CIN, she underwent LEEP of the transformation zone.

The dysplasia was classified by the pathologists in the usual manner and defined as follows: mild dysplasia meaning the presence of immature (dysplastic) cells present in the lower third of the squamous mucosa, moderate dysplasia in the lower two thirds, severe dysplasia the lower three fourths of the thickness of the mucosa and carcinoma in situ ("CIS") full thickness immaturity. The cases were originally diagnosed by a sign out pathologist. The diagnosis of all cases was verified by the same pathologist for uniformity. In all cases, the pathologist was in agreement with the pathologist that had signed out the case.

In order to assess the purity of the indole-3-carbinol used in this study, high performance liquid chromatography (HPLC) was performed on the bottles labeled "product X" which was the indole-3-carbinol, and on the bottles labeled "product Y" which was the placebo. Each of the product X capsules contained slightly more than 100 milligrams of the indole-3-carbinol per capsule, and no indole-3-carbinol was present in the "product Y" capsule. Design Nutritional Products, Orem, UT, provided the indole-3-carbinol capsules and placebo capsules.

HPV status was assessed in all patients by Hybrid capture assay tests (Digene Diagnostics; Beltsville, MD) for low-risk (HPV types 6, 11, 42, 43, 44) and high-risk (HPV types 16, 18, 31, 33, 35, 45, 51, 52, 56). If the Hybrid capture assay was negative; a follow-up polymerase chain reaction (PCR) analysis was performed using consensus primers shown below for the L-1 region of HPV to confirm HPV positivity. The PCR amplification conditions were optimized using DNA isolated from paraffin embedded control HPV positive cervical cancer specimens prior to analysis of the study patient'samples.

Clean catch urine specimens were obtained from each patient at the initial visit and again at their 4-week visit. 2-hydroxyestrone to 16-alpha-hydrosyestrone ratios were assessed in each urine sample. Ascorbic acid was added to the urine specimens to aid in preservation for accurate analysis. ELISA assays were performed to assess the quantity of 2-hydroxyestrone and 16-alpha-hydroxyestrone in each urine sample, and were reported in ng/ml.

B. Results

Routine pathological evaluation of the study patients showed that none (0 of 10) of the patients in the placebo group had complete regression of their dysplasia, as summarized in Table 1. In contrast, 50.0% (4 of 8) of patients in the 200 mg/day treatment arm and 44.4% (4 of 9) of patients in the 400 mg/day treatment arm had complete regression based on their 12-week biopsy.

Figure 3:
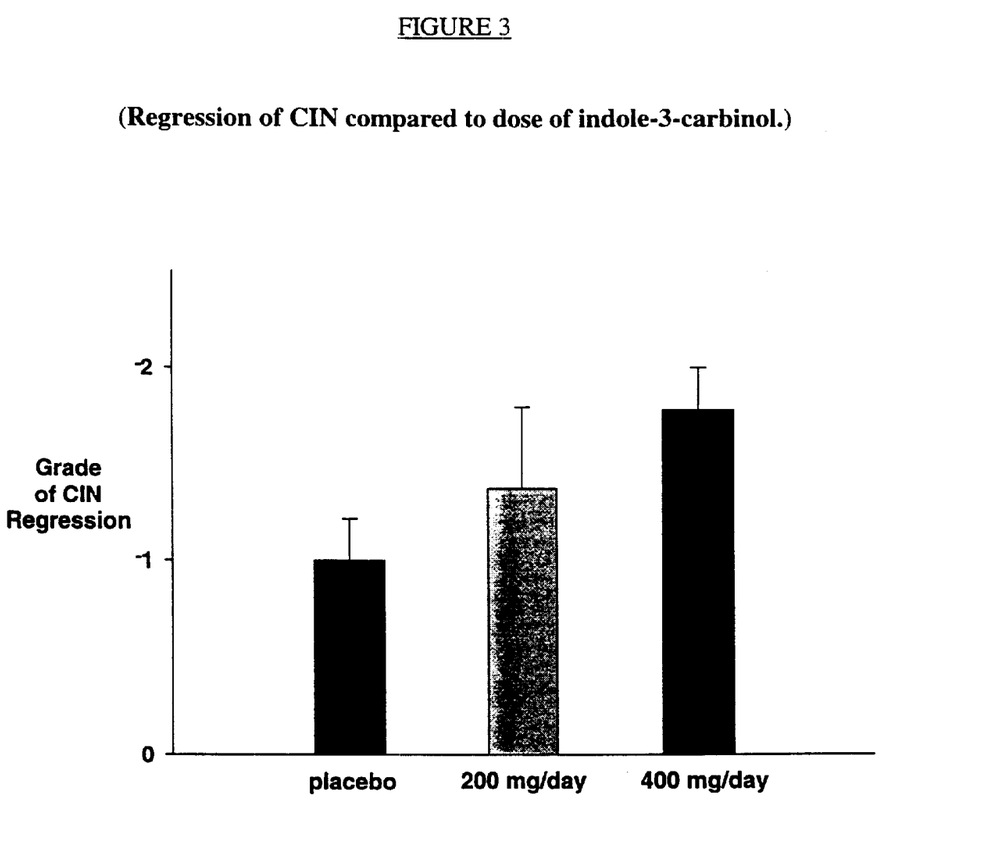
FIG. 3 is a depiction of the data in Table 1.
Figure 4:
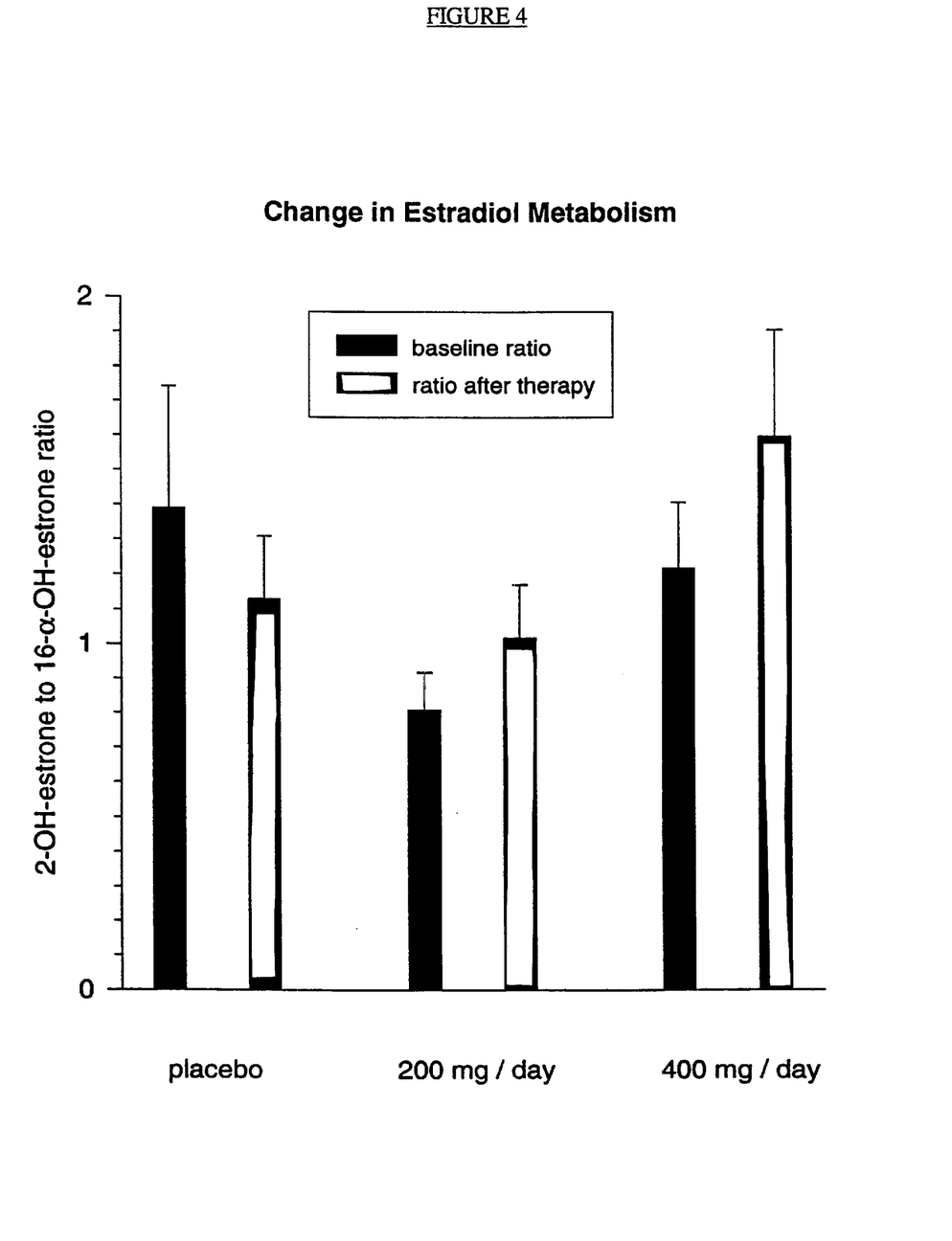
FIG. 4 is a depiction of the data in Table 2.

In order to evaluate the degree of regression between the treatment groups, the mean grade of CIN regression was compared as shown in FIG. 3. A linear dose response relationship was noted between the placebo, 200 mg/day, and 400 mg/day treatment groups. The mean grade change of CIN in the placebo group was a 1.22, the 200 mg/day treatment group was a 1.38, and the 400 mg/day treatment group was a 1.78. Fisher's exact test was used to make comparisons between groups and the significance level was defined as a $p<0.05$. The protective effect of I3C is shown by a relative risk (RR) of 0.50 ((95% CI, 0.25 to 0.99) $p=0.023$) for the 200 mg/day group and a RR of 0.55 ((95% CI, 0.31 to 0.99) $p=0.032$) for the 400 mg/day group.

The urinary 2-hydroxyestrone to 16-alpha-hydroxyestrone ratios were evaluated in each patient at the initiation of the trial and at 4 weeks in order to assess the physiologic response to indole-3-carbinol (Table 2, FIG. 3). Although there was some variability in the individual ratios, a general trend in increase in the ratios was found in the 200 mg/day and 400 mg/day treatment groups before and after therapy (Table 2). In contrast, the placebo treatment group showed a decrease in the ratio before and after therapy.

To determine whether HPV infection alters the response to indole-3-carbinol, HPV status was determined on all patients (Table 1). In the placebo group, 7 of 10 patients had HPV detected. Of these seven placebo patients, 6 had high-risk HPV subtypes (HPV 16 or 18) and one patient had HPV present by PCR, but was not typed. In the 200-mg/day-treatment group, 7 of 8 patients had detectable HPV, and of these, 6 had high-risk subtypes and one patient had HPV present by PCR, but was not typed. In the 400-mg/day treatment group, 8 of 9 patients had detectable HPV, of which 4 were high-risk subtypes and 4 patients had HPV present by PCR, but were not typed. These results show that the incidence of HPV was similar between all treatment groups and historical controls, and suggest that presence of HPV does not correlate with response to indole-3-carbinol.

C. Conclusion

The placebo-controlled trial of indole-3-carbinol in the treatment of CIN demonstrates I3C as a therapeutic. In particular, it demonstrated a physiologic effect of the drug which was seen in a dose-dependent fashion.

Although the invention has been described with regard to certain preferred embodiments and examples, the scope of the invention is to be defined by the appended claims.

What is claimed is:

1. A method of treating cervical or vaginal neoplasia in a mammal comprising administering an effective therapeutic amount of at least one agent selected from the group consisting of indole-3-carbinol and diindolylmethane.

2. The method of claim 1 wherein the mammal is a human and the cervical or vaginal neoplasia is a condition included in the group consisting of cervical intraepithelial neoplasia, intraepithelial neoplasia, vulvar intraepithelial neoplasia and ano-genital warts.

3. The method of claim 2 wherein the agent is indole-3-carbinol.

4. The method of claim 3 wherein the indole-3-carbinol is administered in a dosage in the range of about 2.5 to 20 mg/kg/day.

5. The method of claim 3 wherein the indole-3-carbinol is administered in a dosage in the range of about 200 to 400 mg. per day.

6. The method of claim 3 wherein the indole-3-carbinol is administered orally.

7. The method of claim 2 wherein the agent is diindolylmethane.

8. The method of claim 7 wherein the diindolylmethane is administered in a dosage in the range of about 0.5 to 20 mg/kg/day.

9. The method of claim 7 wherein the diindolylmethane is administered in a dosage in the range of about 50 to 150 mg. per day.

10. The method of claim 9 wherein the diindolylmethane is administered orally.

11. A method of treating cervical intraepithelial neoplasia in a mammal comprising administering an effective therapeutic amount of indole-3-carbinol.

12. The method of claim 11 wherein the mammal is a human.

13. The method of claim 12 wherein the indole-3-carbinol is administered in a dosage in the range of about 2.5 to 20 mg/kg/day.

14. The method of claim 12 wherein the indole-3-carbinol is administered in a dosage in the range of about 200 to 400 mg. per day.

15. The method of claim 13 wherein the indole-3-carbinol is administered orally.

16. The method of claim 14 wherein the indole-3-carbinol is administered orally.

* * * * *

UNITED STATES PATENT AND TRADEMARK OFFICE
CERTIFICATE OF CORRECTION

PATENT NO. : 6,399,645 B1
DATED : June 4, 2002
INVENTOR(S) : Maria Bell et al.

It is certified that error appears in the above-identified patent and that said Letters Patent is hereby corrected as shown below:

<u>Title page,</u>
After Item [57], "4 Drawing Sheets" should read -- 6 Drawing Sheets --;
To drawing sheets, add Tables I and II as per attached.

<u>Column 6,</u>
Line 24, delete "3" and insert -- 5 --.

Signed and Sealed this

Sixth Day of May, 2003

JAMES E. ROGAN
*Director of the United States Patent and Trademark Office*

TABLE 1
DOSE, DIAGNOSIS, AND HPV STATUS

| Patient (#) Dose I-3-C (mg/day) | Diagnosis[1] week 1 | Diagnosis[1] week 12 | Low-risk[2] HPV | High-risk[3] HPV | HPV PCR |
|---|---|---|---|---|---|
| 1. placebo | CIN II | CIN I |  | pos | pos |
| 2. placebo | CIN II | CIN I | neg | neg | neg |
| 3. placebo | CIN II | CIN I | neg | pos |  |
| 4. placebo | CIN III | CIN I | neg | pos |  |
| 5. placebo | CIN III | CIN I | neg | neg | pos |
| 6. placebo | CIN II | CIN I | neg | neg |  |
| 7. placebo | CIN II | CIN I | neg | neg |  |
| 8. placebo | CIN III | CIN III | neg | Pos |  |
| 9. placebo | CIN III | CIN I | neg | Pos |  |
| 10. placebo | CIN III | CIN III | neg | Pos |  |
| 11. 400 | CIN II | CIN I | neg | neg | pos |
| 12. 400 | CIN II | CIN I | neg | pos | pos |
| 13. 400 | CIN III | CIN I | neg | pos |  |
| 14. 400 | CIN II | CIN I | neg | neg | neg |
| 15. 400 | CIN II | normal | neg | neg | pos |
| 16. 400 | CIN III | CIN I | neg | pos | pos |
| 17. 400 | CIN II | normal | neg | neg | pos |
| 18. 400 | CIN III | normal | neg | neg | pos |
| 19. 400 | CIN II | normal | neg | pos |  |
| 20. 200 | CIN III | CIN I |  | pos | pos |
| 21. 200 | CIN II | normal | neg | pos |  |
| 22. 200 | CIN III | CIN III | neg | neg | neg |
| 23. 200 | CIN II | normal | neg | pos |  |
| 24. 200 | CIN III | normal | pos | pos |  |
| 25. 200 | CIN II | CIN II | pos | pos |  |
| 26. 200 | CIN II | normal | neg | neg | pos |
| 27. 200 | CIN II | CIN II | neg | pos |  |

[1]Diagnosis by biopsy
[2]HPV Types 6,11, 42, 43, 44
[3]HPV Types 16,18,31,33,35, 45, 51, 52, 56
List of abbreviations: mg/day – milligrams per day; HPV – human papillomavirus; LEEP – loop electrocautery excision procedure; CIN – cervical intraepithelial neoplasia; neg – negative; pos – positive; PCR – polymerase chain reaction

TABLE 2
2 HYDROXYESTRONE/16-ALPHA-HYDROXYESTRONE RATIO VERSUS DOSE

| Patient (#) and Dose (mg/day) | ratio pretherapy | ratio after I-3-C | ratio % change |
|---|---|---|---|
| 1. placebo | 0.83 | 1.56 | 88 |
| 2. placebo | 1.09 | 1.38 | 26 |
| 3. placebo | 1.26 | 1.91 | 52 |
| 4. placebo | 0.65 | 0.79 | 21 |
| 5. placebo | 0.67 | 0.55 | -18 |
| 6. placebo | 0.57 | 0.64 | 12 |
| 7. placebo | 1.18 | 1.43 | 21 |
| 8. placebo | 3.48 | 0.36 | -89 |
| 9. placebo | 2.80 | 1.58 | -44 |
| 10. placebo | ND | ND | ND |
| 11. 400 | 1.52 | 1.42 | -0.07 |
| 12. 400 | 1.31 | 0.67 | -48 |
| 13. 400 | 0.48 | 0.87 | 81 |
| 14. 400 | 2.44 | 2.85 | 17 |
| 15. 400 | 0.61 | 1.10 | 80 |
| 16. 400 | 1.18 | 3.43 | 190 |
| 17. 400 | 1.42 | 1.45 | 0.02 |
| 18. 400 | 1.13 | 1.51 | 33 |
| 19. 400 | 0.89 | 1.06 | 19 |
| 20. 200 | 0.92 | 1.08 | 17 |
| 21. 200 | 0.69 | 0.69 | 0 |
| 22. 200 | 0.29 | 0.47 | 62 |
| 23. 200 | 1.08 | 0.66 | -39 |
| 24. 200 | 0.55 | 1.37 | 149 |
| 25. 200 | 0.70 | 0.91 | 30 |
| 26. 200 | 0.90 | 1.30 | 44 |
| 27. 200 | 1.32 | 1.66 | 26 |

US006399645C1

(12) EX PARTE REEXAMINATION CERTIFICATE (5236th)
United States Patent
Bell et al.

(10) Number: US 6,399,645 C1
(45) Certificate Issued: Nov. 22, 2005

(54) CHEMOPREVENTION AND TREATMENT OF CERVICAL OR VAGINAL NEOPLASIA

(75) Inventors: Maria Bell, 562 Tolland Dr., Castle Rock, CO (US) 80104; Delf-Christian Schmidt-Grimminger, 562 Tolland Dr., Castle Rock, CO (US) 80104

(73) Assignees: Maria Bell, Castle Rock, CO (US); Delf-Christian Schmidt-Grimminger, Castle Rock, CO (US)

Reexamination Request:
No. 90/006,665, Jun. 2, 2003

Reexamination Certificate for:
Patent No.: 6,399,645
Issued: Jun. 4, 2002
Appl. No.: 09/531,031
Filed: Mar. 20, 2000

Certificate of Correction issued May 6, 2003.

(51) Int. Cl.$^7$ ...................... A61K 31/40; A61K 31/405
(52) U.S. Cl. ........................................ 514/414; 514/415

(56) References Cited

U.S. PATENT DOCUMENTS 6,086,915 A 7/2000 Zeligs

OTHER PUBLICATIONS

Baugh SM et al., "Treatment of cervical dysplasia with indole–3–carbinol" in The Ray A. Barlow Scientific Symposium, Jan. 23, 1998, Shreveport : The Center for Excellence in Cancer Research, Treatment and Education, Louisiana State University Medical Center, Shreveport (LA), p. 3.

Bell, MC et al., "Placebo–controlled Trial of Indole–3–Carbinol in the Treatment of Cervical Dysplasia", Mar. 1999, Gynecol. Oncol. 72:446.

Yuan F et al., "Prevention of Papillomavirus initiated cancer by the phytochemical Indole–3–Carbinol", Proceedings of the 17$^{th}$ International Papillomavirus Conference, Jan. 9–15, 1999, p. 73.

BioResponse–DIM Indolplex Product Information Brochure, Dec. 15, 1998.

Dec. 1998 Bioresponse Letter, Dec. 29, 1998.

Zeligs MA, "Diet and Estrogen Status: The Cruciferous Connection", 1998, J Med Food, 1:67–82.

Ponten J and Guo Z, "Precancer of the Human Cervix", 1998, Cancer Surveys 32:201–229.

Cancer Medicine 3rd edition, 1993, JF Holland ed., Lea & Febiger, Malvern, PA p. 1633.

Molecular Biology of the Cell 2$^{nd}$ ed., 1989, Alberts, B et al., Garland Publishing, Inc., New York, pp. 1193–1194, 1204–1206.

Arbeit, JM et al., "Chronic estrogen–induced cervical and vaginal squamous carcinogenesis in human papillomavirus type 16 transgenic mice", Apr. 1996, Proc Natl Acad Sci, USA 93:2930–2935.

Bell, MC et al., "Placebo–Controlled Trial of Indole–3–Carbinol in the Treatment of CIN", 2000, Gynecologic Oncology, 78:123–129.

*Primary Examiner*—Christopher S. F. Low (57) ABSTRACT

The invention relates to non-surgical methods for treating cervical or vaginal neoplasia including cervical intraepithelial neoplasia, intraepithelial neoplasia, vulvar intraepithelial neoplasia and ano-genital warts. The treatment, which utilizes an effective amount of indole-3-carbinol and/or diindolylmethane, is effective whether or not the patient is also infected with human papillomavirus, the most common sexually transmitted viral disease in the United States and a known risk factor for both cervical intraepithelial neoplasia and cervical cancer.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–16 are cancelled.

\* \* \* \* \*